United States Patent [19]

Kaplan et al.

[11] Patent Number: 5,767,327
[45] Date of Patent: Jun. 16, 1998

[54] METHOD USING AROMATIC OXIDIZING AGENTS

[75] Inventors: Gregory Kaplan, Columbus; Alexander R. Pokora, Pickerington, both of Ohio

[73] Assignee: Wiley Organics, Inc., Coshocton, Ohio

[21] Appl. No.: 726,765

[22] Filed: Oct. 7, 1996

[51] Int. Cl.$^6$ .................................................. C07C 37/00
[52] U.S. Cl. .................................... 568/730; 568/327
[58] Field of Search ........................ 568/367, 730, 568/376

[56] References Cited

U.S. PATENT DOCUMENTS 4,098,830  7/1978  Rutledge ........................... 568/730
4,447,850  5/1984  Kershner ........................... 568/730

OTHER PUBLICATIONS

CA;109:210578: Abst of Tetrahedron Letters, 1988, 29(6) 677–80, Pelter, 1988.

Primary Examiner—Alan L. Rotman
Assistant Examiner—Jean F. Vollano
Attorney, Agent, or Firm—Thompson Hines & Flory LLP

[57] ABSTRACT

A method for oxidizing certain aromatic compounds such as biphenols using an oxidizing agent such as peroxide in a solvent such as a concentrated alkanoic acid or and alkane diol.

25 Claims, No Drawings

METHOD USING AROMATIC OXIDIZING AGENTS

BACKGROUND OF THE INVENTION

The present invention relates to a method for oxidizing certain aromatic compounds using aromatic oxidizing agents such as quinones or diphenoquinones and, more particularly, to a method for producing biphenols by oxidatively coupling phenols.

Japanese Patent 04-154739 A2 to Kitamura et al. discloses a method for producing diphenoquinones by oxidizing a bisphenol using oxoacids. More specifically, this reference discloses oxidizing bisphenol using nitric acid and ferric nitrate as the oxidizing agent. This method is relatively inconvenient, due to the use of nitric acid, and is relatively expensive.

Japanese Patent No. 04-338347 A2 to Inaba et al. discloses a method for producing 4,4'-biphenols via diphenoquinones by oxidizing a phenol with a metal under caustic conditions to form a diphenoquinone and reducing the resulting diphenoquinone with the phenol to produce the 4,4'-biphenol. The problem with this method is that after each step, the metal contaminants need to be washed out and extracted from the mixture and the mixture needs to be neutralized. Furthermore, the yields with this process are at best 85%.

Another method of producing diphenoquinones is disclosed in an article by Nishino et al. entitled "Choice of manganese (III) complexes for the synthesis of 4,4'-bisphenyldiols and 4,4'-diphenoquinones", Bull. Chem. Soc. Jpn., 65(2), 620-2 (Eng) 1992. This reference teaches using manganese (III) acetate to oxidize 2,6-disubstituted phenols to produce the corresponding 4,4'-diphenoquinone.

Stark, B. P. Ph.D. Dissertation, CAMBRIDGE, 1958, discloses using horseradish peroxidase and peroxide to oxidize 2,6-dimethylphenol to 3,3',5,5'-tetramethyldipheno-4,4'-quinone.

Prior methods for producing diphenoquinones exhibited contamination problems and produced diphenoquinones of relatively low purity and yield, were unsafe and were relatively expensive.

Accordingly, there is a need for a clean, convenient and relatively inexpensive method for producing high purity biphenols in satisfactory yields.

SUMMARY OF THE INVENTION

While quinones and diphenoquinones are very effective oxidizing agents, they have been relatively expensive or inconvenient to synthesize. It has been found that when biphenols are dissolved in an alkanoic acid or alkane diol solvent they can be easily oxidized to diphenoquinones using peroxide or oxygen. In addition to being useful in oxidizing biphenols, the reaction can also be used to oxidize dihydroxybenzenes to quinones and to oxidize dianilines to the corresponding imine.

The reaction is particularly useful in designing oxidation processes using diphenoquinones as an aromatic oxidizing agent for oxidatively coupling phenols. In one reaction scheme, a biphenol starting material is dissolved in acetic acid and hydrogen peroxide is added to the solution to oxidize the biphenol to diphenoquinone. The diphenoquinone is used in a coupling reaction in which it oxidizes a phenol and generates biphenol. In this reaction, the diphenoquinone is reduced to the biphenol. A portion of the biphenol is recovered as end product while another portion is recycled to regenerate the diphenoquinone for use in further oxidation reactions.

The process of regenerating and recovering the biphenol and generating the corresponding diphenoquinone, as illustrated above, is also useful in conjunction with a variety of other oxidation reactions in which diphenoquinones are employed as aromatic oxidizing agents. The process provides a convenient, cost effective and industrially useful means to continuously regenerate the spent aromatic oxidizing agent.

DETAILED DESCRIPTION OF THE INVENTION

In accordance with the present invention, a compound having the formula (I), (II) or (III):

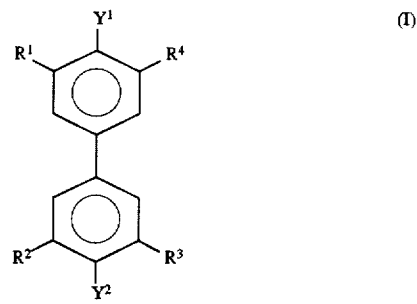

(I)

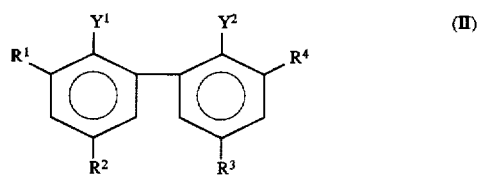

(II)

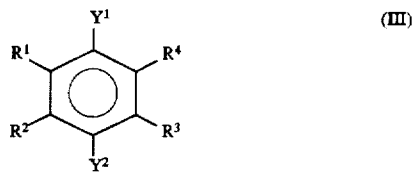

(III)

where $Y^1$ and $Y^2$ are the same or different and represent $OR^5$ or $NH_2$, where $R^5$ represents hydrogen, an alkyl group having 1 to 6 carbon atoms or a phenyl group, and $R^1$–$R^4$ represent alkyl (e.g., C1–C4 alkyl), alkoxy (e.g., C1–C4 alkoxy), aryloxy (e.g., phenoxy), formyl, phenyl, hydrogen, and other groups which are not strongly electron withdrawing, is dissolved in a high boiling solvent (e.g., a solvent that boils at over 100° C.) and oxidized with a peroxide or oxygen. Preferably, $R^1$–$R^4$ are alkyl groups selected from the group consisting of methyl, ethyl, isopropyl, t-butyl groups or combinations thereof.

The solvent used in the invention is preferably selected from the group consisting of alkanoic acids having 1 to 8 carbon atoms and alkane diols having 1 to 8 carbon atoms. While higher homologues can be used unless they are solids, in many cases they are malodorous. The solvent is preferably used neat, i.e., concentrated, but small amounts of water (e.g., up to 30%) may be present. By way of example, acetic acid, propionic acid, ethylene glycol and propylene glycol can be used as the solvent. Preferably, concentrated acetic acid or concentrated propionic acid is used as the solvent. The reaction is preferably carried out at a pH in the range of about 2 to 5.

The oxidation reaction produces water and an aromatic oxidizing agent (e.g., diphenoquinone, a quinone or an imine) of the formula Ia, IIa or IIIa.

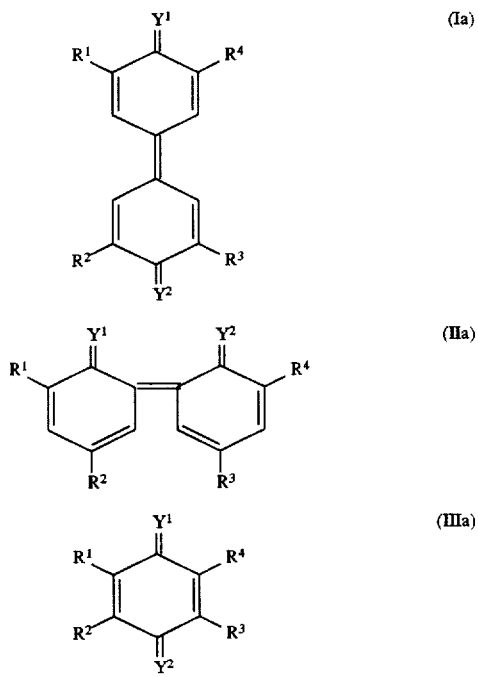

wherein $Y^3$ and $Y^4$ are =O or =NH.

In accordance with the invention, the compound is oxidized by an oxidizing agent selected from the group consisting of a peroxide or oxygen. Preferably, the oxidizing agent is a peroxide and, preferably, hydrogen peroxide, but other peroxides such as methyl peroxide, ethyl peroxide, etc. are also useful. The peroxide is typically reacted in approximately a stoichiometric amount. In the preferred embodiment of the invention, the solvent is acetic acid and in acetic acid, the peroxide has a life time that is limited. Accordingly, from the standpoint of efficient use of the peroxide, excess peroxide is avoided. It is desirable to dissolve the peroxide in water in a concentration of about 1 mM to 10M and then add it to the reaction medium at a rate which decreases as the biphenol reacts and is converted to the quinone and the amount of biphenol present in the reaction medium in turn decreases. In total, the peroxide is reacted in approximately a stoichiometric amount.

Where the compound that is oxidized is a biphenol, the concentration of the biphenol in the solvent is typically in the range of up to about 3 to 4 pounds per gallon of acid, i.e., up to 50% solids by weight. Those skilled in the art will readily be able to identify suitable concentrations for compounds of the formula II and III. The reaction is generally carried out at a temperature of about 80° to 150° C. Temperatures over about 150° C. are avoided when using peroxide because at these high temperatures, the peroxide itself decomposes. At lower temperatures in the range, the reaction proceeds more slowly unless a stronger acid is added.

In accordance with one embodiment of the invention, the aromatic oxidizing agent is produced in the presence of about 0.05 to 2%, preferably 0.25%, of a strong acid selected from the group consisting of para-toluene sulfonic acid, methane sulfonic acid, sulfuric acid, and phosphoric acid. Nitric acid, hydrochloric acid and mineral acids may also be used. Without desiring to be bound, it is believed that the acid may catalyze production of atomic oxygen. The presence of the strong acid increases the rate of reaction. For example, little or no reaction occurs at 100° C. unless an acid is added.

In accordance with a particular embodiment of the invention, an oxidizing agent prepared as above is used to oxidize a compound having the formula (IV) or (V):

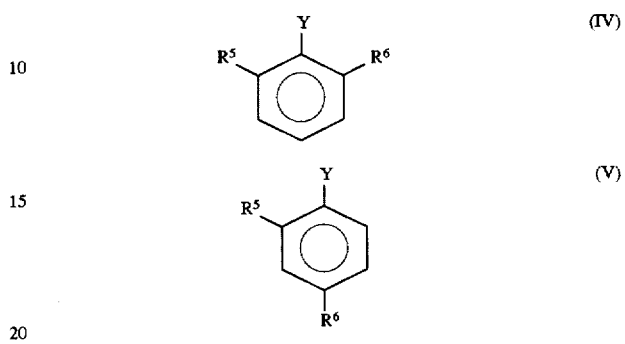

where Y is OH or $NH_2$, $R^5$ and $R^6$ represent alkyl (e.g., C1–C4 alkyl), alkoxy (e.g., C1–C4 alkoxy), aryloxy (e.g., phenoxy), formyl, phenyl, and other groups which are not strongly electron withdrawing. This reaction can be carried out by adding the compound of formula IV or V to the solution containing the oxidizing agent of the formula Ia, IIa, or IIIa. Generally, the oxidizing agent and the oxidized compound will be used in stoichiometric amounts or the oxidizing agent will be employed in a slight excess. The reaction is generally carried out at a temperature in the range of about 120° to 150° C. Typically, the reaction proceeds to completion in about 2 hours.

In a particular embodiment of the invention a phenol of the formula IV or V is added to an oxidized biphenyl of the formula I or II under conditions such that the phenol is oxidatively coupled to form a biphenol. This reaction is illustrated in Equation 1 for the case in which the compound of formula I is a biphenol and the compound of formula IV is 2,6-dimethylphenol.

Equation 1

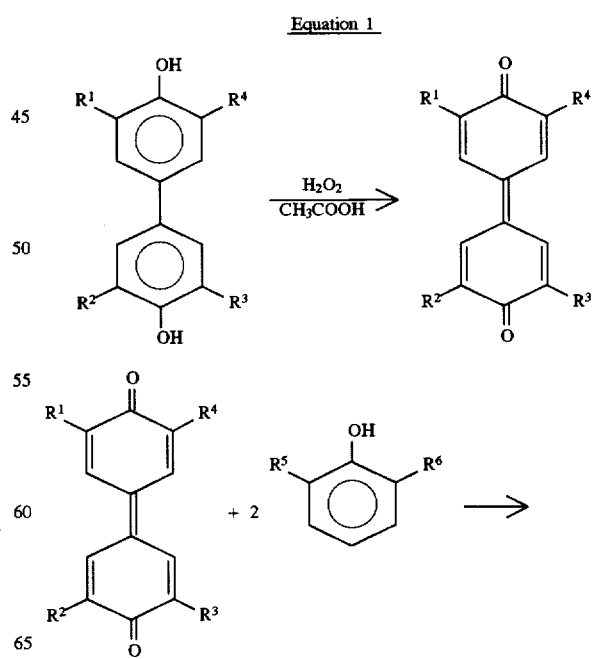

-continued
Equation 1

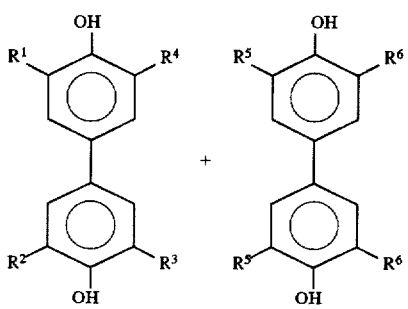

In this particular embodiment of the invention, a 4,4'-biphenol is oxidized to produce a 4,4'-diphenoquinone. The 4,4'-diphenoquinone oxidizes a 2,6-disubstituted phenol to form an oxidatively coupled biphenol (2,2',6,6'-tetrasubstituted-4,4'-biphenol) and regenerate the initial 4,4'-biphenol as the reduction product of the diphenoquinone. Thus, the reaction yields biphenols by two routes, namely, reduction of the diphenoquinone and the oxidative coupling of the phenol. If the substitution of the phenol and the diphenoquinone is the same, the biphenol products will be the same. In this case, it is advantageous to recover a portion (e.g., about half) of the biphenol as product and to react the remaining portion with peroxide to regenerate the diphenoquinone which is useful in oxidatively coupling additional phenol. The biphenol can be readily separated because by cooling the solution, it separates from the solution as a precipitate. It will be readily seen that this method is convenient, cost effective and advantageous for use in industry because, by recovering the biphenol, the diphenoquinone can be regenerated conveniently without employing the metal oxidizing agents and alkaline conditions conventionally used by industry.

When the substitutions of the phenol and the diphenoquinone are different, the reduction product of the diphenoquinone and the oxidation product of the phenol can be separated and the regenerated biphenolic reduction product can be recovered and reacted to generate the diphenoquinone. The biphenol can be separated from the oxidation reaction medium for regeneration in accordance with the invention using conventional separation and recovery techniques such as filtration, crystallization, extraction, chromatography, precipitation, etc.

While the discussion herein has focused on the regeneration of biphenol, processes for oxidizing compounds with aromatic oxidizing agents of the formulas Ia, IIa, and IIIa and regenerating the reduction products are also within the scope of the invention. Those skilled in the art will appreciate that the process of the present invention can be used in conjunction with the oxidation of any compound which can be oxidized by the aromatic oxidizing agents. For example, tetrasubstituted diphenoquinones can be used in a conventional manner to oxidize a variety of materials. Among the oxidation reactions in which they may be used in addition to the oxidation of a 2,6-disubstituted or a 2,4-disubstituted phenol to a biphenol are the oxidation of aniline to polyaniline and the oxidative polymerization of phenol to form a phenolic oligomer.

Those skilled in the art can easily identify other examples of oxidizable compounds based on a comparison of the redox potential of the oxidizable compound and the redox potential of the diphenoquinone or quinone and other factors commonly used in identifying redox pairs. Examples of other compounds that can be oxidized in accordance with the teachings herein include phenols substituted at the 4-position with an alkyl group, an amino group, a cyano group, a nitro group, a 4-hydroxyphenylsulphono group or a benzotriazoyl group.

The methods of the present invention can also be implemented in the preparation of unsubstituted biphenol. Equation 1 above yields a tetrasubstituted biphenol. To prepare unsubstituted biphenol, tetra-t-butylbiphenol can be dealkylated. The t-butyl groups can be removed in a conventional manner. For example, 2,2',6,6'-tetra-t-butyl-4,4'-Biphenol is dissolved in p-cresol and heated to a temperature greater than 180° C. in the presence of toluene sulfonic acid or mineral acid. Isobutylene is released and biphenol is collected. The isobutlyene can be recovered and reacted with phenol to make the di-t-butylphenol from which the biphenol can be prepared.

The following non-limiting examples illustrate the invention in more detail.

EXAMPLE 1

Preparation 2,2',6,6',-tetra-t-butyl-4,4'-Diphenoquinone 55 grams of 2,2',6,6'-tetra-t-butyl-4-4'-biphenol were dissolved in 150 ml of acetic acid at 120° C. 12 ml of 35% solution of hydrogen peroxide were added over a period of 2 hours. The reaction mixture was cooled, filtered and dried. 48 grams of 2,2',6,6'-tetra-t-butyl-4-4'-diphenoquinone were recovered.

EXAMPLE 2

2,2',6,6'-tetra methyl-4,4'-Diphenoquinone 120 gram of 2,2',6,6'-tetramethyl-4,4'-biphenol were mixed with 400 ml of acetic acid at 80°-100° C. 48 ml of 35% solution of hydrogen peroxide were added over a period of 90 minutes. The reaction mixture was cooled, filtered and dried. 63 grams of 2,2',6,6'-tetramethyl-4,4'-diphenoquinone were collected.

EXAMPLE 3

A mixture of 24 g (0.1 mol) of 3,3',5,5'-tetramethyldipheno-4,4'-quinone obtained in Example 2 and 52 g (0.25 mol) of 2,4-di-t-butylphenol was boiled in 150 ml of water for 4 hours. The reaction mixture was filtered and dried. Formation of 2,2',6,6'-tetramethyl-4,4'-biphenol and 4,4',6,6'-tetra-t-butyl-2,2'-biphenol was confirmed by GPC and liquid chromatography. 20 g of pure 4,4',6,6'-tetra-t-butyl-2,2'-biphenol were isolated by extraction of hot isooctane and washing by methanol.

EXAMPLE 4

A mixture of 2.5 g of 4,4'-diphenol-sulphone and 3.0 g of 3,3',5,5'-tetramethyldipheno-4,4'-quinone obtained from the biphenol in Example 2 was heated at 250° C. for 10 minutes. Formation of a polymer (4,4'-diphenol/sulphone polymer) and 2,2',6,6'-tetramethyl-4,4'-biphenol were obtained by GPC and liquid chromatography.

EXAMPLE 5

A mixture of 24 g (0.1 mol) of 3,3',5,5'-tetramethyldipheno-4,4'-quinone obtained from the biphenol in Example 2 and 30 g (0.24 mol) of 2,4-dimethylphenol was boiled for 2 hours in 150 ml of water. Reaction mixture was filtered and dried. Formation of a polymer and 2,2',6,6'-tetramethyl-2,2'-biphenol were obtained by GPC and liquid chromatography.

Having described the present invention in detail and by reference with the examples and appended claims.

What is claimed is:

1. A method comprising the steps of:

(a) dissolving a substituted biphenyl compound of the formula (I) or (II):

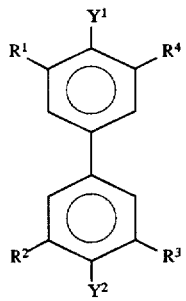
   (I)

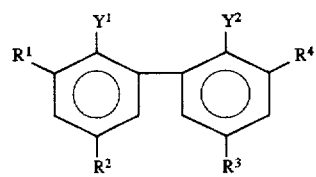
   (II)

where $Y^1$ and $Y^2$ are the same or different and represent $OH$ or $NH_2$, and $R^1$-$R^4$ represent al alkoxy, aryloxy, formyl, phenyl or hydrogen, in a solvent selected from the group consisting of an alkanoic acid and an alkane diol to form a solution of said biphenyl compound; and (b) adding an oxidizing agent selected from the group consisting of peroxide or oxygen to said solution to oxidize said biphenyl compound to form an oxidation product of the formula (Ia) or (IIa):

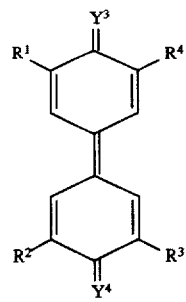
   (Ia)

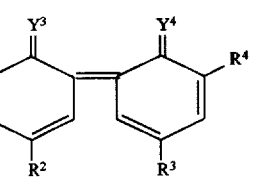
   (IIa)

where $Y^3$ and $Y^4$ are $=O$ or $=NH$ and $R^1$-$R^4$ are defined as in formulas (I) and (II).

2. The method of claim 1 further comprising the step of (c) adding a compound of the formula (IV) or (V):

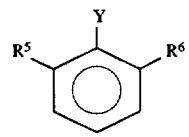
   (IV)

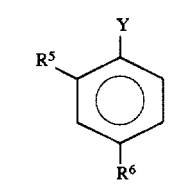
   (V)

where $Y$ is $OH$ or $NH_2$, $R^5$ and $R^6$ represent alkyl, alkoxy, aryloxy, formyl or phenyl to said solution containing said oxidation product, under conditions such that said compound of the formula (IV) or (V) reacts to form an oxidatively coupled product.

3. The method of claim 2 comprising the additional steps of:

(d) removing a portion of said oxidatively coupled product; and (e) repeating said steps (b) and (c).

4. The method of claim 1 wherein said $Y^1$ and $Y^2$ are OH, said oxidizing agent is peroxide, and said solvent is concentrated acetic acid or concentrated propionic acid.

5. The method of claim 1 wherein step (b) is carried out at a temperature of approximately 80° to 150° C.

6. The method of claim 2 wherein step (c) is carried out at a temperature of approximately 120° to 150° C.

7. The method of claim 1 wherein the solution of step (a) contains about 0.05 to 2% of a strong acid selected from the group consisting of para-toluene sulfonic acid, methane sulfonic acid, sulfuric acid, and phosphoric acid.

8. The method of claim 1 wherein $R^1$-$R^4$ are t-butyl.

9. The method of claim 8 wherein said method includes the additional step of dealkylating the oxidatively coupled product recovered in step (d) to form biphenol.

10. The method of claim 3 wherein said step (d) includes cooling the solution to cause said oxidatively coupled product to separate from said solution as a precipitate.

11. A method comprising the steps of:

(a) dissolving a phenyl compound of the formula (III):

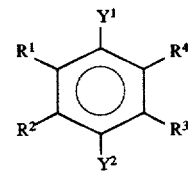
    (III)

where $Y^1$ and $Y^2$ are the same or different and represent OH or $NH_2$, and $R^1$-$R^4$ represent alkyl, alkoxy, aryloxy, formyl, phenyl or hydrogen in a solvent selected from the group consisting of an alkanoic acid and an alkane diol to form a solution of said phenyl compound;

(b) adding an oxidizing agent selected from the group consisting of peroxide or oxygen to said solution of step (a) to oxidize said compound to form an oxidation product of the formula (IIIa):

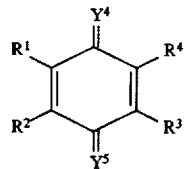

(IIIa)

where $Y^4$ and $Y^5$ are the same or different and represent =O or =NH and $R^1$–$R^4$ are defined as in formula (III); and (c) adding a compound of the formula (IV):

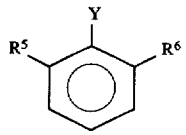

(IV)

where Y is OH or $NH_2$ and $R^5$ and $R^6$ represent alkyl, alkoxy, aryloxy, formyl or phenyl to said solution containing said oxidation product under conditions such that said compound of the formula (IV) reacts to form an oxidatively coupled product.

12. The method of claim 11 comprising the additional steps of:

(d) removing a portion of said oxidatively coupled product; and (e) repeating said steps (b) and (c).

13. The method of claim 11 wherein said $Y^1$ and $Y^2$ are OH, said oxidizing agent is peroxide, and said solvent is concentrated acetic acid or concentrated propionic acid.

14. The method of claim 13 wherein said peroxide is reacted in approximately a stoichiometric amount.

15. The method of claim 11 wherein step (b) is carried out at a temperature of approximately 80° to 150° C.

16. The method of claim 15 wherein step (c) is carried out at a temperature of approximately 120° to 150° C.

17. The method of claim 16 wherein the solution of step (a) further contains about 0.05 to 2% of a strong acid selected from the group consisting of para-toluene sulfonic acid, methane sulfonic acid, sulfuric acid, and phosphoric acid.

18. The method of claim 11 wherein $R^1$–$R^4$ are t-butyl.

19. The method of claim 18 wherein said method includes the additional step of dealkylating the oxidatively coupled product recovered in step (d) to form biphenol.

20. The method of claim 12 wherein said step (d) includes cooling the solution to cause said oxidatively coupled product to separate from said solution as a precipitate.

21. The method of claim 1 wherein $Y^1$ and $Y^2$ are OH and $Y^3$ and $Y^4$ are =O.

22. The method of claim 21 wherein the solution of step (a) further contains about 0.05 to 2% of a strong acid selected from the group consisting of para-toluene sulfonic acid, methane sulfonic acid, sulfuric acid, and phosphoric acid.

23. The method of claim 22 where $R^1$–$R^4$ are t-butyl.

24. The method of claim 2 wherein $Y^1$, $Y^2$ and Y are OH and $Y^3$ and $Y^4$ are =O.

25. The method of claim 24 wherein $R^1$–$R^6$ are t-butyl.

\* \* \* \* \*

UNITED STATES PATENT AND TRADEMARK OFFICE
CERTIFICATE OF CORRECTION

PATENT NO. : 5,767,327
DATED : June 16, 1998
INVENTOR(S) : Gregory Kaplan and Alexander R. Pokora It is certified that error appears in the above-indentified patent and that said Letters Patent is hereby corrected as shown below:

Claim 1, col. 7, line 35, the term "al" should be - - alkyl, - - .

Signed and Sealed this

First Day of September, 1998

Attest:

BRUCE LEHMAN

Attesting Officer

Commissioner of Patents and Trademarks